United States Patent [19]

Dilling

[11] Patent Number: 4,732,572
[45] Date of Patent: Mar. 22, 1988

[54] AMINE SALTS OF SULFOMETHYLATED LIGNIN

[75] Inventor: Peter Dilling, Isle of Palms, S.C.

[73] Assignee: Westvaco Corporation, New York, N.Y.

[21] Appl. No.: 783,781

[22] Filed: Oct. 3, 1985

[51] Int. Cl.$^4$ .......................... C08H 5/02; C09B 67/18
[52] U.S. Cl. ............................................ 8/557; 8/602; 530/501; 530/505; 106/123.1
[58] Field of Search .............................. 530/501, 505; 106/123.1; 8/557, 602

[56] References Cited

U.S. PATENT DOCUMENTS

| | | | |
|---|---|---|---|
| 3,407,188 | 10/1968 | Carvagna | 530/501 |
| 3,505,243 | 4/1970 | Steinberg et al. | 530/500 X |
| 4,444,562 | 4/1984 | Lin | 530/500 X |
| 4,590,262 | 5/1986 | Dilling | 530/501 X |
| 4,629,469 | 12/1986 | Dilling | 530/501 X |
| 4,636,224 | 1/1987 | Dilling | 530/501 X |
| 4,642,336 | 2/1987 | Dilling | 530/501 X |
| 4,670,482 | 6/1987 | Dilling | 530/501 X |

Primary Examiner—Earl Nielsen
Attorney, Agent, or Firm—Terry B. McDaniel; Richard L. Schmalz

[57] ABSTRACT

Disclosed is a method for the production of a sulfomethylated lignin amine salt from the lignin by-product of the black liquor residue of a kraft pulping process and the use of lignin amine salts as additives in other chemical compositions. The lignin amine salt is produced by precipitating lignin from the black liquor and reacting the precipitated lignin slurry with formaldehyde. Thereafter, the lignin slurry is acidified to a pH of about 2 to 3 and water-washed to remove inorganic salts and other impurities therefrom. The washed methylolated lignin is reacted with an organic amine and a sulfur-oxygen-containing compound, such as sulfur dioxide to form the sulfomethylated lignin amine salt.

The sulfomethylated lignin amine salt products are disclosed as an additive in dyestuff and printing ink compositions, as well as a sequestrant in pesticide compositions, with improved results over certain lignin salts heretofore employed as additives in such compositions.

7 Claims, No Drawings

AMINE SALTS OF SULFOMETHYLATED LIGNIN

This invention relates to a method of producing amine salts of lignosulfonates and to products produced thereby, and, more particularly, to sulfomethylated lignin amine salts particularly suited for use as additives in dyestuff and pesticide formulations.

BACKGROUND OF THE INVENTION

Lignin is a complex high-molecular weight polymer occurring naturally in close association with cellulose in plants and trees. Lignin constitutes, on dry weight basis, approximately 27 to 33 percent of the tree in softwoods and approximately 20 to 24 percent in hardwoods. Lignin is amorphous and has a high molecular weight with a tridimensional structural network. Unlike cellulose, lignin is aromatic in nature.

In the paper-making industry, lignin is separated from the cellulose of the wood product by two principal pulping processes known as the sulfite process and the kraft process. In the sulfite pulping process, lignin is separated from the cellulosic portion of the wood pulp by direct sulfonation, while the kraft process is based on an alkaline degradation mechanism causing cleavage of $\beta$-aryl ether linkages in the polymeric lignin which subsequently results in chemical functions of the phenolic type. Kraft lignin is isolated by acid precipitation from the black liquor of the kraft pulping process at a pH below the PKa of the phenolic groups. Purification of the sulfite lignin involves fermentation of residual sugars from the wood to alcohol and the exchange of calcium or magnesium ions to sodium. The kraft process is more widely employed and constitutes about 60% of the worldwide pulping processes employed in the paper-making industry.

Lignin by-products of the black liquor residue of a kraft pulping process employed in the paper-making industry have long been employed as additives in other chemical applications and compositions. The high degree of chemical activity which is characteristic of lignins permits the preparation of many novel and economical organic derivatives. Typical reactions which lignins can undergo are hydrogenation, halogenation, nitration, sulfonation, oxygenation, salt formation, etherification, and esterification. Lignin is a naturally occurring polymer characterized by a series of closely linked benzene rings carrying methoxyl, hydroxyl, and other substitute groups. Lignin by-products variously have been employed as additives in various chemical compositions as a surfactant, extender, dispersant, reinforcement, absorbent, binder, sequestering agent, emulsifier and emulsion stabilizer, and as a stabilizing and protective colloid. Lignosulfonate compounds, particularly sodium salts of lignosulfonates, have been employed as additives and dispersants in textile dyestuffs and printing pigments. Such lignin by-products have been sold for several years under the trademarks Indulin ®, Reax ®, and Polyfon ® by Westvaco Corporation of North Charleston, S.C.

In the kraft pulping process, lignin is obtained as a by-product from the spent pulping liquor, known as black liquor, where lignocellulosic materials, such as wood, straw, cornstalks, bagasse, and the like are processed to separate the cellulosic pulp from the lignin. In kraft pulping, the wood is subjected to the effects of strong alkali wherein the lignin forms a soluble sodium salt in the alkaline region which is separated from the cellulose and dissolves in the pulping liquor. The lignin is then recovered from the black pulping liquor by reducing the pH of the same.

Reduction in the pH of black liquor containing soluble lignin salts generally may be accomplished by introduction of carbon dioxide which converts the phenolic hydroxyl groups on the lignin molecule, which are in ionized form, into their free phenolic or acidic form. This conversion renders the lignin insoluble in the black liquor and, as a result, it precipitates out. To precipitate the alkali lignin from the black liquor as water-insoluble products, the pH of black liquor initially having a pH around 13 is lowered to a pH of about 10.5 at which point the lignin begins to precipitate. The lignin precipitate can be further purified by reducing the pH level to about pH 2 where the lignin is coagulated and washed with water to remove inorganic salts and other impurities and obtain a lignin product designated a "A" lignin. Such products are sold under the name and trademark INDULIN ® "A" by Westvaco Corporation.

Lignin obtained from the kraft, soda, or other alkaline processes is not recovered as a sulfonated product, but is sulfonated, if desired, by reacting the material with a bisulfite or sulfite compound. Sulfonated lignins are understood to be lignins containing at least an effective amount of sulfonate groups to give water-solubility in moderately acid and higher pH solutions.

One conventional process for sulfonating kraft process lignins involves sulfomethylation of the alkali lignin by reacting the lignin with sodium sulfite and formaldehyde. Such a process is described in Adler, et al. U.S. Pat. No. 2,680,113. Sulfomethylation acts upon the aromatic phenolic nuclei of the lignin mulecule in such a manner that —$CH_2SO_3H$ groups are bonded to the aromatic ring. It is also possible to sulfonate the lignin side-chain of the aromatic nucleus by sodium sulfite treatment of the lignin in the absence of formaldehyde. Sulfomethylation of the alkali lignin has generally been carried out at a pH level of 9.0 or higher in order to ensure optimum phenol ionization and solubility of the lignin for sulfomethylation.

More recently, it has been proposed to sulfomethylate kraft process lignins in a two-step operation wherein the ionized phenol component of the lignin is methylolated at an alkaline pH by the addition of an aldehyde, the pH is lowered to an acidic pH to precipitate the methylolated lignin to wash the precipitate to remove undesired inorganic salts, and the lignin is thereafter sulfonated by addition of a sodium or ammonium salt of a sulfur and oxygen-containing compound. Such processes are described in commonly assigned co-pending U.S. patent application Ser. Nos. 06/657,973 and 06/679,901, filed Oct. 5, 1984 and Dec. 10, 1984, and now U.S. Pat. Nos. 4,590,262 and 4,642,336, issued May 20, 1986 and Feb. 10, 1987, respectively. Such sodium and ammonium lignosulfonates find use as additives and dispersants in dye compositions and the like.

In the sulfite pulping process, the lignin in the wood undergoes hydrolysis and in situ sulfonation allowing it to become soluble. A variety of commercial sulfite pulping processes exist today and their names reflect the conditions of pulping applied. Among the sulfite processes are the magnesium base pulping process, the calcium base process, the ammonia base process, the soda, the neutral, the bisulfite, and acid sulfite processes. Sulfonation of lignin during the sulfite pulping process takes place in the side chain involving either the terminal alcohol group or the sulfonic acids attach themselves on the carbon of the side chain of the aromatic nucleus. Sulfite lignins are sulfonated during the pulping process in which sodium or calcium bisulfite is used as the cooking chemical. They become water-soluble and thus can be easily washed from the cellulosic pulp.

It has been proposed to employ sodium salts of lignosulfonates as a sequestrant in liquid pesticide formulations; however, their use has been restricted to very low loading levels since higher levels of the sodium lignin salt causes an ion-exchange reaction in amine-containing pesticides with resultant sludging and precipitation in the pesticide liquid composition. Amine salts of ethylene diamine tetraacetic acid (EDTA) and citric acid also have been traditionally used as sequestrants, but their manufacture and use is quite costly.

U.S. Pat. No. 3,784,493 discloses the manufacture of amine lignosulfonates from spent sulfite liquor of the sulfite pulping process which are reacted with formaldehyde to produce products useful as setting control agents in cement, as hydration shale inhibitors in oil well drilling muds, and as fillers in the formation of resins.

SUMMARY OF THE INVENTION

The present invention is directed to production of a sulfomethylated lignin amine salt from the lignin by-product of the black liquor residue of a kraft pulping process and to the use of lignin amine salts as additives in other chemical compositions. The lignin amine salt is produced by lowering the pH of the black liquor residue from an initial pH level of around 13 to around 10.5 to 9, at which point the lignin precipitates from the black liquor. The precipitated lignin slurry is reacted with an aldehyde compound to methylolate the same, after which the lignin slurry is acidified to a pH of about 2 to 3 where it is water-washed to remove inorganic salts and other impurities therefrom.

The methylolated lignin is thereafter reacted with an organic amine and a sulfur-oxygen-containing compound, such as sulfur dioxide, preferably at a pH of around 6.3 to 6.5, to form the sulfomethylated lignin amine salt.

The sulfomethylated lignin amine salt products of the present invention may be employed effectively as an additive in dyestuff and printing ink compositions, as well as a sequestrant in pesticide compositions, with improved results over certain lignin salts heretofore employed as additives in such compositions.

DETAILED DESCRIPTION OF PREFERRED EMBODIMENTS

The above as well as other objects of the present invention will become more apparent and the invention will be better understood from the following detailed description of preferred embodiments thereof. As mentioned above, the sulfomethylated lignin amine salts of lignosulfonates of the present invention may be prepared from lignin recovered from the black liquor residue of a kraft pulping process. The amine salts, when employed as additives in dyestuff compositions, exhibit less color interference and fiber-staining than the sulfomethylated lignin sodium salts of the prior art. The amine salts are low foaming, and may be used with sensitive azo dye compositions with less color reduction than the lignin sodium salts. In printing ink compositions, the amine salts of the present invention exhibit desired low electrical conductivity and a high print gel viscosity with synthetic-type thickeners.

The lignin amine salts of the present invention further can be used as effective additives in acid and direct dye compositions containing amine components, where sodium and ammonium salt lignins heretofore have not been effective.

The lignin amine salts also exhibit improved results when used a sequestrants in pesticide formulations, particularly in pesticide formulations containing amine components, where the lignin sodium and ammonium salts undergo ion exchange and cause precipitation problems.

The sulfomethylated lignin amine salts of the present invention may be produced from the black liquor residue of a kraft pulping process by the following method steps:

(1) The black liquor residue having an initial pH of around 13 is treated with an acidifying compound, such as carbon dioxide, to reduce the pH to around 9.5, at which point the lignin precipitates.

(2) The precipitated lignin is solubilized by adjusting the pH to 11.0 with alkali and treated with an aldehyde compound, such as formaldehyde, to methylolate the same.

(3) The methylolated lignin is acidified to a pH of around 2 to 3 to further precipitate and coagulate the same.

(4) The precipitated methylolated lignin is water-washed to remove inorganic salts, undesired reactants and other impurities.

(5) The methylolated, purified lignin is treated with an organic amine compound and a sulfur-oxygen-containing compound to form the sulfomethylated lignin amine salt.

The chemical reaction of the above-described method of production of the lignin amine salt may be expressed as follows:

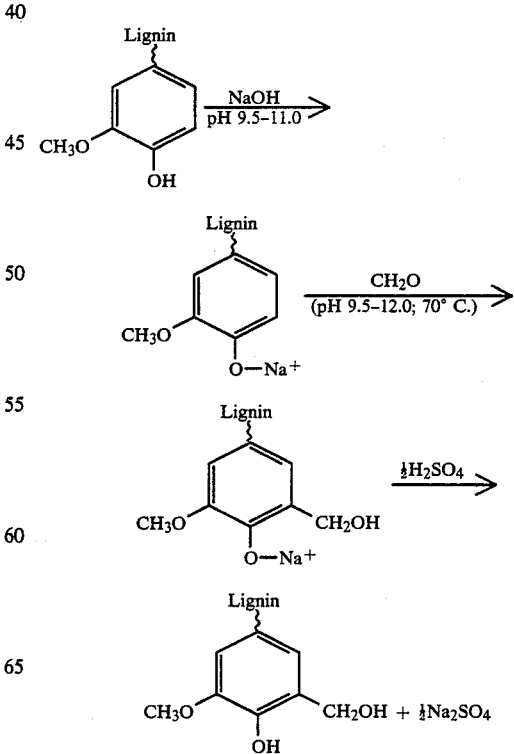

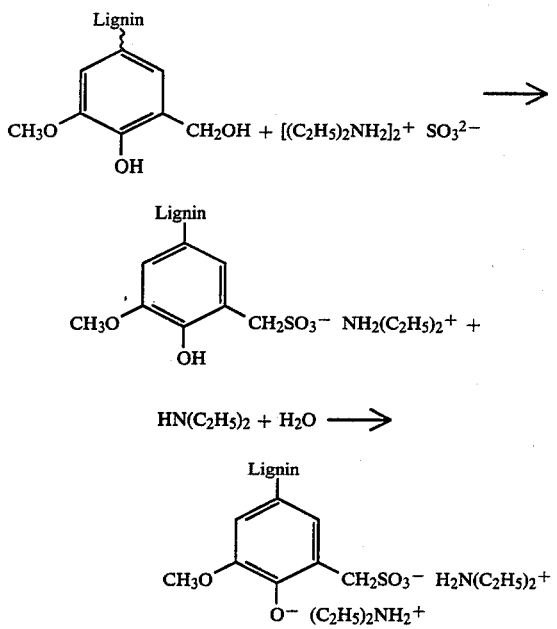

Treatment of the purified, methylolated lignin with the organic amine and a sulfur-oxygen-containing compound may be carried out by (1) forming an amine sulfite compound which is then reacted with the methylolated lignin, or (2) by adding the amine to an aqueous methylolated lignin slurry, at a particular starting pH, and by back titration with $SO_2$ gas in an amount to bring the slurry to a specified pH.

Although the sulfonation reaction can be conducted over a broad pH range, a starting pH of 6.3 to 6.5 is preferred to ensure a product pH close to the neutral point, and to avoid excessive pH adjustment in preparing the lignin product for a particular end use.

Organic amine compounds which may be employed in preparation of the lignin amine salts of the present invention include trimethylamine, triethylamine, triethanolamine, diethanolamine, dimethylamine, monoethanolamine, propylene diamine, cyclohexylamine, diethylene tetramine, tetraethylene pentamine, and others.

Preferably, the precipitated lignin slurry is treated with the aldehyde compound to methylolate the same at a pH of approximately 11. Although a number of aldehyde compounds might be employed, formaldehyde is preferred.

The following laboratory procedure illustrates a preferred method of preparing the sulfomethylated lignin amine salts of the present invention from the black liquor of a kraft pulping process. Although the methylolation step employs three moles of formaldehyde, and three moles of $SO_2$ are employed for the sulfonation step (based on 1,000 grams of lignin), other molar ratios of these components can be employed with satisfactory results. For example, if it is desired to have a lower sulfonation level, the amounts of the aldehyde and the sodium sulfur-oxygen containing compounds could be reduced accordingly.

Laboratory Procedure

A. Methylolation of Lignin (1) Solid lignin recovered from the black liquor of a pulping process by treatment with $CO_2$ is slurried to a 25% total solids content.
(2) The pH of the slurry is adjusted to 11.0 with a 50% sodium hydroxide (NaOH) solution to solubilize the lignin.
(3) Three moles of formaldehyde (HCHO) per 1,000 grams lignin are added and the lignin solution reacted for two hours between 30° C.–80° C., preferably at 70° C.
(4) The solution is acidified to a pH of 2 with a 25% sulfuric acid solution ($H_2SO_4$) to precipitate the lignin.
(5) The precipitated lignin is heat coagulated to 85° C., cooled to room temperature, filtered, and water washed free of inorganic matter.

B. Formation of Amine Salt of Lignosulfonate (1) 100 grams of the above methylolated lignin cake on a 100% solids basis is slurried to 25%.
(2) The slurry is adjusted with triethanolamine to a pH of around 6.3.
(3) 2.5 moles of triethanolamine and 2.5 moles $SO_2$ are added to the methylolated lignin.
(4) The pH is again adjusted to 6.3 by addition of triethanolamine.
(5) The temperature of the lignin is raised to 95° C. and maintained for about 1 to 20 hours, preferably between 8 and 12 hours, to form the sulfomethylated lignin amine salt.

The sulfonation reaction can be conducted at atmospheric pressure at a temperature of around 80°–100° C., preferably at about 95° C., or at elevated pressures above 100° C., up to about 190° C., preferably at about 120°–140° C. Atmospheric pressure conditions are preferred since pressure reaction above 100° C. tends to cause a color increase in the lignin product, the higher the temperature the darker the lignin color. This degradation or darkening in color reflects itself in higher fiber staining characteristics during the dyeing cycle to produce duller color shades.

The following examples and tabulated data are presented to illustrate benefits and advantages of the present invention.

EXAMPLE I

Sulfomethylated lignin amine salts prepared from kraft pulping liquors generally in accordance with the laboratory procedure set forth above were tested for fiber staining, dye color reduction, foaming, electrical conductance, heat stability, and viscosity. The results obtained were compared in certain instances with similarly prepared sulfomethylated lignin sodium salt.

For viscosity measurements, each sulfonated lignin salt was adjusted to 25% solids and heated to about 70° C. and a glacial acetic acid was added slowly until a pH of 7.0 was obtained. The liquid compositions were temperature adjusted to 25° C. A Brookfield viscometer (Model LVT) was employed for all measurements.

For heat stability measurements, dye/lignin salt compositions were prepared from lignin amine salts of the present invention. Compositions consisting of 50 grams of dyestuff, 35 grams of the sulfomethylated lignin salt, 125 milliliters of water, and 5 drops of ethylenediaminetetracetic acid (1% solids at pH 10.0–10.5) were prepared and the pH of each composition adjusted to 8.0 with acetic acid. In instances where the pH of the product was below pH 8, no pH adjustments were made. Each dye composition containing a lignin additive was ground in a ball mill to the point where the filter test for disperse dyes was passed. To 1 gram of each solid dye composition was added 250 milliliters of water, the solution boiled for fifteen minutes, and then filtered through a tared Watman filter paper no. 2 above a no. 4 paper (with vacuum), as specified in the standard American Association of Textile Chemists and Colorists (AATCC) heat stability test. The time for the filtration was recorded, the filter paper dried, and the residual dye material remaining on the filter was calculated by weight and visually observed.

For lignin dispersion measurements, dye lignin salt compositions were prepared in accordance with the procedures for heat stability measurements set forth in the preceding paragraph, except that the water and dye composition mixture was not heated, but was slurried, and then filtered through the filter paper arrangement indicated. The time for completion of the filtration of the aqueous dye composition was recorded.

Fiber staining tests of the lignin products were carried out by measuring light reflectance of nylon fiber to which lignin product compositions having a pH of 4.0 had been applied in a 1 to 1 weight ratio.

Printing gel viscosities are measured by the following test procedure. Eight grams of each prepared sulfomethylated lignin product is dissolved in 160 ml. of water, and the pH adjusted to 7.0 with a 25% solution of sulfuric acid. Thirty grams of a Carbopol printing paste gel manufactured by BASF is mixed into 810 ml. of water using a high speed mixer. The lignin solution is slowly added to the gel under mixing conditions. Viscosity measurements are calculated using a Brookfield viscometer Model LVT. Viscosities above 10,000 are considered acceptable in a printing paste application.

Electrolyte content of the various sulfomethylated lignin products are determined by adding 10 grams of the lignin product to 1,000 ml. of water. The pH was adjusted to 7.0 and the solution was added to an Amicon Laboratory Ultra-Filtration System, Model M 2000 which contained a 500 molecular size membrane. The membrane allows molecular weights below 500, e.g., inorganic salts, to go through it while the lignin constituents are retained by the membrane. Nitrogen is used under pressure as a carrier gas. After the volume inside the ultra-filtration apparatus has decreased to 100 ml., deionized water was added to 1,000 ml. This sequence was repeated until the conductance of eluent corresponded with the conductance of the water. The concentrate inside the ultra-filtration chamber was removed, the water evaporated, and the residue was dried. The difference in the weight amount of the residue and the 10 grams of lignin product originally employed corresponds to the inorganic salt present in the sample.

Conductance measurements were obtained as follows. A 5% lignin product solution was prepared in water. The pH was adjusted to 8.0 with dilute sulfuric acid. If the product pH was at or below 8.0, no adjustments were made. The conductivity of the product was then determined by a conductance meter Model 31 manufactured by Yellow Springs Instrument Company.

Color degradation tendencies are determined in accordance with an azo dye color reduction test procedure wherein a standard diazo dispersed dye slurry is prepared by mixing one gram of C.I. Dispersed Blue 79 in one liter of distilled water. One gram of a lignin salt composition to be tested and compared is placed into 125 ml. of water and 100 ml. of the dye slurry is added thereto. The pH is adjusted to 5.0 to 5.5 and 5 grams of a prescoured Dacron (Type 54) yarn skein is added and placed in a Renigal Dye Control Machine, Model PR, which is heated to 80° C. After 15 minutes, the temperature is raised to 130° C. and held at this temperature for 45 minutes (15 minutes is required to reach the temperature of 130° C.). At the end, the autoclave is cooled and the skein removed, washed with tap water, and dried. Color reduction is determined by reflectance measurements utilizing a photoelectric reflection meter (Model 610) manufactured by the Photovolt Corporation of New York. The degree of color reduction is calculated on the basis of reflectance values and is expressed in percent color loss.

Results of the various tests on lignin salts of the prior art and the present invention are present in the following tables:

Fiber staining on wool and nylon with lignosulfonate thiethanolamine salts of the present invention were compared to lignosulfonate sodium salt counterparts. Fiber staining was determined by way of light reflectance measurements with 5 grams of lignin applied to 5 grams of fiber. Higher reflectance numbers, in percentage of reflectance, indicate brighter color.

| | FIBER STAINING | | | |
|---|---|---|---|---|
| | Staining on Nylon | | Staining on Wool | |
| | pH 4 | pH 7 | pH 4 | pH 7 |
| Triethanolamine Salt | 71% | 82% | 62% | 78% |
| Sodium Salt | 50% | 59% | 27% | 45% |

Color degradation tendencies were compared with the amine and sodium salts of the lignosulfonates in accordance with the azo dye color reduction test procedures outlined above. The results are indicated in the following table:

| THE EFFECT OF AZO DYE COLOR REDUCTION USING A TRIETHANOLAMINE AND A SODIUM SALT OF A LOW SULFONATED LIGNOSULFONATE IN THE PRESENCE AND ABSENCE OF OXYGEN AT DIFFERENT pH LEVELS | | | | |
|---|---|---|---|---|
| | Color Reduction | | | |
| | In the Presence of Air | | In the Absence of Air | |
| | Amine Salt (%) | Sodium Salt (%) | Amine Salt (%) | Sodium Salt (%) |
| pH 4 | 7.0 | 39.0 | 7.9 | 39.0 |
| pH 5 | 6.9 | 46.0 | 8.0 | 72.4 |
| pH 6 | 7.1 | 73.0 | 7.9 | 79.0 |
| pH 7 | 7.1 | 96.0 | 7.9 | 100.0 |
| pH 8 | 33.9 | 96.0 | 89.0 | 100.0 |

Foaming of the lignosulfonate amine salts of the present invention were compared with lignosulfonate sodium salts, with the results being indicated in the following chart:

| FOAMING TENDENCIES OF A TRIETHANOLAMINE (TEA) AND A SODIUM SALT OF A LOW SULFONATED LIGNIN AT pH 4 | | |
|---|---|---|
| | Triethanolamine Salt | Sodium Salt |
| Initial foam | 30 ml. | 80 ml. |
| 60 Sec. | broke in 58 Sec. | 80 ml. |

| FOAMING TENDENCIES OF A TRIETHANOLAMINE (TEA) AND A SODIUM SALT OF A LOW SULFONATED LIGNIN AT pH 4 -continued | | |
|---|---|---|
| | Triethanolamine Salt | Sodium Salt |
| 120 Sec. | — | 80 ml. | determined by preparing a 2% aqueous solution of the lignosulfonate amine salt, adding $H_2SO_4$ (50% sol.) slowly until the product begins to precipitate as observed by a cloudy appearance of the product in solution. The results thereof are presented in the following table:

| SOLUBILITY AND VISCOSITY OF VARIOUS AMINE SALTS OF LIGNOSULFONATES | | | | | | | | |
|---|---|---|---|---|---|---|---|---|
| Amine Type | Amts. of $CH_2O$ for Methylol. (Moles/ 1,000 g Lignin) | Moles of Amine/$SO_2$ per 1,000 g Lignin | Temp of React. (°C.) | React. Time (Hrs.) | St. pH | Final pH | Precip. Point (2% Solution) | Visc in cps (25% Solution, pH 7, 25° C.) |
| $(CH_3)_3N$ | 1.3 | 1.5/1.5 | 95 | 16 | 7.5 | 7.5 | 1.49 | 15.5 |
| $(CH_3)_2NH$ | 1.3 | 2.0/2.0 | 95 | 16 | 7.5 | 9.25 | 1.40 | 12.0 |
| $(CH_3)_2NH$ | 1.3 | 1.5/1.5 | 95 | 16 | 7.5 | 9.0 | 1.43 | 17.3 |
| $(CH_3)_2NH$ | 1.3 | 1.0/1.0 | 95 | 16 | 7.5 | 8.75 | 2.15 | 35.0 |
| $(C_2H_5)_3NH$ | 1.3 | 2.0/2.0 | 95 | 16 | 6.5 | 7.3 | 1.39 | 10.3 |
| $(C_2H_5OH)NH_2$ | 1.3 | 2.0/2.0 | 95 | 16 | 6.5 | 7.4 | 1.42 | 10.0 |
| $(C_2H_5OH)_2NH$ | 1.3 | 1.5/1.5 | 95 | 16 | 6.3 | 7.0 | 1.52 | 15.8 |
| $(C_2H_5OH)_3N$* | 3.0 | 2.1/2.1 | 95 | 16 | 6.3 | 7.6 | 1.41 | 11.0 |
| $(C_2H_5OH)_3N$* | 3.0 | 3.0/3.0 | 140 | 2 | 6.3 | 7.2 | 1.10 | 8.5 |

*(Sulfonation ingredients formed in situ with lignin. In all other cases, amine sulfite formed separately, then combined with methylolated lignin.)

Electrical conductivity and printing gel viscosity data were determined for the various lignosulfonate amine salts and compared to sodium lignosulfonate salt, the results of which are indicated in the following table:

| CONDUCTIVITY AND PRINTING GEL VISCOSITY DATA ON VARIOUS LIGNOSULFONATE AMINE SALTS | | | |
|---|---|---|---|
| Amine Type | Moles of $CH_2O$/ 1,000 g Lignin | Moles of Amine Sulfite/ 1,000 g Lignin | Conductivity ($\mu$ mhos) At 5% Lignin Conc. | Printing Gel Viscosity (cps) |
| $(CH_3)_2NH$ | 1.3 | 1.0 | 4,875 | 24,000 |
| $(CH_3)_2NH$ | 1.3 | 1.5 | 5,650 | 23,000 |
| $(CH_3)_2NH$ | 1.3 | 2.0 | 7,800 | 17,000 |
| $(CH_3)_3N$ | 1.3 | 1.5 | 4,575 | 27,500 |
| $(C_2H_5OH)_3N$* | 3.0 | 2.1 | 2,290 | 41,000 |
| $(C_2H_5OH)_3N$* | 3.0 | 3.0 | 2,725 | 29,000 |
| Sodium Salt | 1.0 | 1.0 $Na_2SO_3$ | 9,800 | 1,800 |

*(Sulfonation ingredients formed in situ with lignin. In all other cases, amine sulfite formed separately, then combined with methylolated lignin.)

Heat stability performance of amine salts of lignosulfonate as dispersants in dyestuffs were determined and the data collected is presented in the following table:

| HEAT STABILITY PERFORMANCE OF AMINE SALTS OF LIGNOSULFONATE DISPERSANTS | | | | | | | |
|---|---|---|---|---|---|---|---|
| Type of Amine Salt | Moles of Reactants/ 1,000 g of Lignin | | Temp. of Reaction (°C.) | Dispersion (Ambient) Filter Residue in mg | | Heatstability (Filter) Residue in mg | |
| | $CH_2O$ | Amine/$SO_2$ | | Red I | Blue 118 | Red I | Blue 118 |
| Triethanolamine | 3.0 | 2.1 | 95 | 3.9 | 5.4 | 7.9 | 11.5 |
| Triethanolamine | 3.0 | 3.0 | 140 | 4.6 | 3.7 | 8.4 | 9.3 |
| Diethanolamine* | 1.3 | 1.5 | 95 | 2.5 | 4.5 | 5.6 | 9.5 |

*(Amine sulfite formed before combining with lignin. In all other cases, sulfonation ingredients formed in situ with lignin.)

Solubility and viscosity tests were conducted on a number of various sulfomethylated lignin amine salts produced in accordance with the present invention. The precipitation points of the various amine salts are A sulfomethylated lignin amine salt of the present invention was employed as a sequestrant in a 2,4-D liquid pesticide formulation of the following composition:

| PESTICIDE COMPOSITION COMPONENT | % BY WEIGHT |
|---|---|
| (1) 2,4-D dimethyl amine pesticide (45% acid equivalent) | 56.7% |
| (2) dimethyl amine lignosulfonate | 1.0% |
| (3) water | 42.3% |

The amine salt sequestrant performs exceptionally well while use of comparable sodium and ammonium salts of sulfomethylated lignins are unsatisfactory due to ion exchange reaction between the lignin salt and the amine-containing components of the 2,4-D pesticide composition.

EXAMPLE II

Lignin amine salts were prepared from MARASPERSE CB sold by Reed Ltd. which is a sodium lignosulfonate salt by-product of a bisulfite pulping process. The amine salts were prepared as follows: To two hundred-fifty grams of fully active cation exchange resin (DOWEX HCR-S) manufactured by Dow Chemical was added twenty-five grams of a 10% MARASPERSE CB lignin solution. The amounts were calculated to permit removal of the sodium ion and replacement with a hydrogen ion. The pH decreased during the ion exchange procedure from pH 8.25 to pH 1.75. After separating the ion exchange resin by filtration and washing the resin with 100 mL of water, the lignosulfonate was pH adjusted to 7.0 with an appropriate amine compound, thus displacing the hydrogen ion with the amine. After concentration of the product to 25% solids content, the lignin amine salts were compared to the commercial sodium salt of lignin Marasperse CB for conductivity, Azo dye reduction, dispersion, and heat stability, in accordance with procedures set forth herein. The results of these comparisons are set forth in the data in the following tables.

CONDUCTANCE VALUES OF VARIOUS AMINE SALTS OF MARASPERSE CB IN RELATION TO ITS COMMERCIAL SODIUM SALT FORM

| Product Types | Conductance in m mhos (5% Solution, pH 7.0) |
| --- | --- |
| MARASPERSE CB (Sodium Salt) | 8,000 |
| MARASPERSE CB Triethanolamine Salt | 3,880 |
| MARASPERSE CB Diethanolamine Salt | 4,400 |
| MARASPERSE CB Monoethanolamine Salt | 6,110 |
| MARASPERSE CB Triethylamine Salt | 4,500 |

AZO DYE REDUCTION OF VARIOUS AMINE SALTS OF MARASPERSE CB IN RELATION TO ITS COMMERCIAL SODIUM SALT FORM

| Product Types | 1 g Lignin Product/ 0.1 g Dye (pH 5) | 2 g Lignin Product/ 0.1 g Dye (pH 5) |
| --- | --- | --- |
| MARASPERSE CB Sodium Salt (Control) | 41% (violet tint) | 63% (violet tint) |
| MARASPERSE CB Triethanolamine Salt | 0 | 11% |
| MARASPERSE CB Diethanolamine Salt | 0 | 14% |
| MARASPERSE CB Monoethanolamine Salt | 14.6% | 45% |
| MARASPERSE CB Triethlamine Salt | 9.5% | 39% |

DISPERSION AND HEAT STABILITY DATA

| | Dispersion (Filtration Time- Sec.) | | Heat Stability (Filter residue- mg) | |
| --- | --- | --- | --- | --- |
| | Red I | Blue | Red I | Blue |
| MARASPERSE CB (Sodium salt) | 11.5 | 10.5 | 13.1 | 21.5 |
| MARASPERSE CB (Triethanol amine salt) | 11.0 | 11.9 | 14.2 | 19.4 |
| MARASPERSE CB (Monoethanol amine salt) | 11.6 | 11.6 | 12.9 | 22.6 |

The above data indicates that the amine salts of sulfite-base lignosulfonates are distinctly different from their sodium salt counterparts.

From the foregoing description, examples, and tabulated data, it can be seen that the amine salts of lignosulfonates of the present invention are particularly adapted for use in dyestuff formulations, printing pastes, and pesticide compositions. It is contemplated that the salts of the present invention may also be applicable as additives in cement, concrete, coal slurries, ceramic materials, inks, oil drilling compositions, and the like. Specifically, it is contemplated that they may be employed as retarders and accelerators in gypsum wall boards, cement and concrete, as viscosity thinners and stabilizers in coal and dye applications, as dispersants and grinding aids in inks, additives for oil well drilling, and as a soil enhancer in agriculture.

That which is claimed is:

1. A method of producing amine salts of lignosulfonates, particularly suited for use as additives in other chemical compositions, comprising the steps of:
   (a) ionizing the phenol component of a lignin material in alkaline liquid medium;
   (b) methylolating the lignin material in the ortho position of the phenol component;
   (c) lowering the pH of the liquid to an acid pH to precipitate the methylolated lignin material;
   (d) washing the precipitated lignin material with water to remove inorganic salts and residual reactants therefrom; and
   (e) reacting the washed, purified methylolated lignin material with an amine compound and a sulfur-oxygen-containing compound in liquid medium to produce sulfomethylated lignin amine salt.

2. A method as defined in claim 1 wherein the washed, purified methylolated lignin material is reacted with the amine and sulfur-oxygen-containing compound in liquid medium by first adding the amine compound to the lignin in liquid medium at a pH of around 6 to 7, and the sulfur-oxygen-containing compound is thereafter added to the lignin amine composition in sufficient amount to sulfonate the composition and form the sulfomethylated lignin amine salt at a pH of about 6 to 7.

3. A method as defined in claim 2 wherein the amine is selected from the group consisting of trimethylamine, triethylamine, triethanolamine, diethanolamine, dimethylamine, and monoethanolamine, propylene diamine, cyclohexylamine, diethylene tetramine, tetraethylene, and pentamine.

4. A method as defined in claim 3 wherein the sulfur-oxygen-containing compound is sulfur dioxide gas.

5. A method as defined in claim 1 wherein the purified methylolated lignin material is reacted with the amine and sulfur-oxygen-containing compound to form the amine salt by first reacting the amine and sulfur-oxygen-containing compound to form an amine sulfite, and thereafter reacting the amine sulfite with the lignin to form the sulfomethylated lignin amine salt.

6. A method as defined in claim 1 wherein the sulfur-oxygen-containing compound is added to the amine/methylolated lignin composition at a pH of about 6.3 to 6.5.

7. An improved dyestuff composition containing as an additive therein the sulfomethylated lignin amine salt of claim 1.

* * * * *